US008535691B2

(12) United States Patent
Shaffer et al.

(10) Patent No.: US 8,535,691 B2
(45) Date of Patent: Sep. 17, 2013

(54) PERFLUROCHEMICAL TREATMENT PROCESS AND APPARATUS

(75) Inventors: Thomas H. Shaffer, Chadds Ford, PA (US); Robert G. Stern, Tucson, AZ (US); Marla R. Wolfson, Wyndmoor, PA (US)

(73) Assignee: Peach Technologies, LLC., Philadelphia, PA (US)

( * ) Notice: Subject to any disclaimer, the term of this patent is extended or adjusted under 35 U.S.C. 154(b) by 1780 days.

(21) Appl. No.: 11/276,180

(22) Filed: Feb. 16, 2006

(65) Prior Publication Data

US 2007/0190082 A1 Aug. 16, 2007

(51) Int. Cl.
*A61K 9/00* (2006.01)

(52) U.S. Cl.
USPC .......................................................... 424/400

(58) Field of Classification Search
None
See application file for complete search history.

(56) References Cited

U.S. PATENT DOCUMENTS

| | | | | | |
|---|---|---|---|---|---|
| 4,105,798 | A | | 8/1978 | Moore et al. | |
| 4,110,474 | A | | 8/1978 | Lagow et al. | |
| 4,187,252 | A | | 2/1980 | Lagow et al. | |
| 4,289,499 | A | | 9/1981 | Clark, Jr. et al. | |
| 4,366,169 | A | * | 12/1982 | White | 514/755 |
| 4,375,812 | A | * | 3/1983 | Vaseen et al. | 604/290 |
| 4,378,797 | A | * | 4/1983 | Osterholm | 604/24 |
| 4,443,480 | A | | 4/1984 | Clark, Jr. | |
| 4,657,532 | A | * | 4/1987 | Osterholm | 604/24 |
| RE33,451 | E | * | 11/1990 | Clark, Jr. | 514/628 |
| 5,007,927 | A | * | 4/1991 | Badylak et al. | 623/3.12 |
| 5,284,663 | A | * | 2/1994 | Speaker | 424/489 |
| 5,447,002 | A | * | 9/1995 | Wehrmann | 52/239 |
| 5,514,720 | A | | 5/1996 | Clark, Jr. et al. | |
| 5,635,539 | A | | 6/1997 | Clark, Jr. et al. | |
| 5,674,913 | A | | 10/1997 | Clark, Jr. | |
| 5,684,050 | A | | 11/1997 | Clark, Jr. et al. | |
| 5,741,248 | A | * | 4/1998 | Stern et al. | 606/21 |
| 5,824,703 | A | | 10/1998 | Clark, Jr. | |
| 5,840,767 | A | | 11/1998 | Clark, Jr. | |
| 5,961,988 | A | * | 10/1999 | Zastrow et al. | 424/400 |
| 6,343,225 | B1 | | 1/2002 | Clark, Jr. | |
| 6,500,192 | B1 | * | 12/2002 | Werding | 606/201 |
| 2003/0120204 | A1 | * | 6/2003 | Unger et al. | 604/82 |
| 2003/0131844 | A1 | * | 7/2003 | Kumar et al. | 128/200.24 |
| 2003/0215392 | A1 | * | 11/2003 | Lanza et al. | 424/9.32 |
| 2006/0253089 | A1 | * | 11/2006 | Lin | 604/301 |

OTHER PUBLICATIONS

Aulick et al. (Am J Physiol Heart Circ Physiol.1977; 233: H520-H526).*

Wolfson et al., Liquid-assisted ventillation: an alternative respiratory modality (Pediatric Pulmonology 26: 42-63 (1998)).*

Magnotti et al., Gut-Derived Mesenteric Lymph (Arch. Surg., 134, 1333-1341, 1999).*

Definition of “closed” from dictionary.com, accessed on May 23, 2011.*

T. Iwai, et al., A new treatment for ischemic ulcers: foot bath therapy using high oxygen soluble fluid. J. Cardiovasc Surg. (Torino) May-Jun. 1989: 30(3): 490-3. (Abstract).

* cited by examiner

*Primary Examiner* — David J Blanchard
*Assistant Examiner* — Tigabu Kassa
(74) *Attorney, Agent, or Firm* — Paul & Paul

(57) ABSTRACT

A subject is confined in a closed environment at an elevated pressure through which perfluorochemical fluid containing dissolved oxygen is circulated to treat disease or injury.

17 Claims, 2 Drawing Sheets

PERFLUROCHEMICAL TREATMENT PROCESS AND APPARATUS

BACKGROUND OF THE INVENTION

1. Field of the Invention

The present invention relates to a process to promote the viability, sustainability and growth of living cells, and in particular, for the treatment of an area of the body affected by disease or injury, and apparatus for effecting the process.

2. Brief Description of the Prior Art

Wounds and tissue injuries constitute a very large grouping of medical conditions including ischemic ulcers, traumatic injuries thermal injuries, and mechanical musculoskeletal injuries (including but not limited to skin, muscle, cartilage, ligament, and tendon injuries).

A wide variety of skin disorders can also be included, such as psoriasis, atopic dermatitis, skin infections including bacterial, fungal, and viral diseases, and post viral processes such as shingles.

Additionally, a wide variety of disease processes and injuries affect visceral organs and other internal structures throughout the body.

While it is difficult to quantify all the skin diseases, ulcers, burns, sprains, and other injuries that occur in the population, they are believed to occur in many millions of patients in the United States alone. For example, in a Canadian study, 1.8% of the population was determined to have open or healed ulcers of the lower extremity. Extrapolation of this data results in an estimated 5.3 million such patients in United States alone, which is likely conservative given the considerably higher rate of diabetes and peripheral vascular disease in the United States. Similarly, in a literature review from 1987, over one million people per year sought medical attention each year in the United States for ankle sprains alone. Low back pain is another perhaps more far-reaching example given the elusive nature of current treatment strategies to resolve this chronic condition. Thus, this would presumably be an exceedingly conservative estimate of current conditions, given the growth of exercise in the youth and adult population as well as the preponderance of patients who do not seek physician attention for their less significant injuries. Adding the number of skin diseases, burn injuries, traumatic wounds, and other wounds and tissue injuries yields estimates in the tens of millions of wound and tissue injury patients in the United States alone each year.

The healing of ischemic and other wounds and tissue injuries is promoted by the delivery of adequate oxygenation to the affected areas.

A variety of techniques are used by doctors and physical therapists to deliver oxygen and thus promote such healing. These include revascularization of areas with interrupted blood flow (via surgical bypass or endovascular therapy), drug therapy, and local warming (via direct heat application or ultrasound) to increase local perfusion and improve oxygen delivery.

Hyperbaric therapy has also been used for direct delivery of oxygen to tissue sites via a pressurized, oxygenated environment to treat wounds.

Perfluorochemical (PFC) liquids have been used to deliver oxygen systemically via the lungs and as an artificial blood substitute. In addition, the anti-inflammatory nature of PFC liquids and vapors when used in cell and in vivo conditions has been demonstrated. A fluorocarbon liquid has been used in a bath environment to partially treat foot ulcers. T. Iwai et al, "A new treatment for ischemic ulcers: foot bath therapy using high oxygen soluble fluid," J. Cardiovasc. Surg. (Torino) 1989 May-June; 30(3): 490-3.

There is a continuing need for methods for promoting the healing of areas of the body affected by wounds or disease, and in particular for a method for treating ischemic ulcers, traumatic injuries, thermal injuries, and mechanical musculoskeletal injuries.

SUMMARY OF THE INVENTION

In one aspect, the present invention provides a process to promote the healing of an area of the body of any subject living organism, such as a mammal, bird or reptile, or portion thereof (such as an organ, tissue or cell) affected by an injury or disease. In the process of the present invention, the subject is put into a closed environment, and a perfluorochemical fluid is provided in the closed environment. In the present process, a selected gaseous material is dissolved in the perfluorochemical fluid, and the subject is immersed in the perfluorochemical fluid in which the selected gaseous material is dissolved. In the process, the pressure within the closed environment is adjusted to differ from the atmospheric pressure. Preferably, the perfluorochemical fluid is circulated through the closed environment.

Thus, in one aspect the present invention provides a process to promote the healing of an area of the body of a living organism affected by an injury or disease. This process comprises confining the affected area in a closed environment, and providing a perfluorochemical fluid in the closed environment. In this process, oxygen is dissolved in the perfluorochemical fluid to oxygenate the perfluorochemical fluid, and a pressure differing from atmospheric pressure is provided in the closed environment. In this process, the affected area is treated by immersing the area in the oxygenated perfluorochemical fluid.

In one aspect of this process, the pressure inside the closed environment is varied according to a pressure variation predetermined program. Preferably, the temperature inside the closed environment is controlled, and in one aspect of the present process, the temperature inside the closed environment is varied according to a predetermined temperature variation program.

Preferably, in this process the atmosphere of the closed environment is pressurized to greater than atmospheric pressure in order to oxygenate the perfluorochemical fluid. Preferably, the atmosphere of the closed environment is pressurized to greater than about 106 kPa, and more preferably to greater than about 111 kPa.

In another embodiment of the present process, the atmosphere in the closed environment is pressured to less than atmospheric pressure in order to promote extraction of carbon dioxide by the perfluorochemical fluid from the affected area. In this embodiment of the present process, it is preferred that the atmosphere in the closed environment is pressurized to less than about 96 kPa, and more preferably to less than about 91 kPa.

In another embodiment of the present process, the atmosphere in the closed environment is alternately pressurized to a first pressure and a second pressure. In one aspect of this embodiment, it is preferred that the first pressure is greater than atmospheric pressure and the second pressure is less than atmospheric pressure. Preferably, in this aspect the first pressure is greater than about 106 kPa and the second pressure is less than about 96 kPa. In another aspect of this embodiment, it is preferred that the first pressure is a pressure greater than atmospheric pressure and the second pressure is atmospheric pressure. Preferably, in this aspect, the first pressure is greater than about 96 kPa.

Preferably, in this process the perfluorochemical fluid is warmed to a temperature greater than the body temperature of the subject, preferably, to a temperature greater than about 38 degrees Celsius in the case of a human subject.

In another aspect of the process of the present invention, it is preferred to provide a biologically active material in the perfluorochemical fluid. Preferably, the biologically active material is selected from the group consisting of tissue growth promoters, hormones, antibiotics, genetic delivery systems, and therapy delivery systems.

Preferably, in the present process the perfluorochemical fluid is provided in a fluid form selected from the group consisting of liquid, nebulized phases, vaporized phases, and aerosolized phases.

Preferably, in the present process the perfluorochemical fluid comprises at least one fluorinated hydrocarbon having at least one-half of the corresponding hydrocarbon's hydrogen atoms substituted by fluorine. Preferably, the at least one fluorinated hydrocarbon is selected from the group consisting of $C_4F_9CH{=}CH_4C_9$, i-$C_3F_9CH{=}CHC_6F_{13}$, $C_6F_{13}CH{=}CHC_6F_{13}$, $C_{10}F_{18}$, $C_8F_{17}Br$, $(C_6F_{13})_2O$, $CF_3CFOCF_2CF_3$, $(CF_3)_2CFO(CF_2)_3CF_3$, $(CF_3)_2CFO(CF_2)_4OCF(CF_3)_2$, $(CF_3)_2CFO(CF_2)_6OCF(CF_3)_2$, F-2-butyltetrahydrofuran, F-n-cyclohexylpyrrolidine, F-n-methyldecahydroquinoline, F-n-methyldecahydroisoquinoline, F-adamantane, F-methyladamantane, F-1,3-dimethyladamantane, F-dimethylbicyclo[3,3,1]nonane, F-trimethylbicyclo[3,3,1]nonane, F-tripropylamine, F-tributylamine, C-4 alkyl decalins $C_{14}F_{24}/C_{14}F_{26}$, $C_{10}F_{18}$, $C_8F_{17}Br$, $C_6F_{14}$ perfluorohexanes, and mixtures thereof. In yet another aspect of the process of the present invention, electrically charged particles are provided in the perfluorochemical fluid. In this aspect, the electrically charged particles are preferably provided by circulating the perfluorochemical fluid through a microfiltration membrane.

In another aspect of the process of the present invention, magnetically charged particles are provided in the perfluorochemical fluid.

In another embodiment of the present invention, a second gas is dissolved in the perfluorochemical fluid to enhance the oxygenation of the perfluorochemical fluid. Preferably, the second gas is selected from the group consisting of helium, nitric oxide, carbon monoxide, and other potentially therapeutic gases.

In another aspect of the process of the present invention, ultrasound is transmitted through the liquid perfluorochemical fluid to the affected area. Preferably, the frequency of the ultrasound is selected from those employed in established practice for physical therapy of soft tissue or organ injuries.

In one presently preferred embodiment of the process of the present invention, the entire body of the subject living organism is confined in the closed environment while the proving suitable respiration means to the organism. In another presently preferred embodiment of the process of the present invention, a portion of the body of the subject living organism is confined to the closed environment.

In one aspect the process of the present invention, the affected area of the body is located on an extremity of the body, such as a foot having an ischemic ulcer.

The process of the present process invention can be effected using apparatus including a treatment chamber for confining at least a portion of the living organism in a closed environment and a reservoir for perfluorochemical fluid. The apparatus further includes a first conduit for transferring the perfluorochemical fluid between the reservoir and the treatment chamber. Such an apparatus further includes at least one injection port for providing a selected gaseous material, such as oxygen or carbon dioxide in the perfluorochemical fluid, and a compressor for increasing the pressure of the perfluorochemical fluid to increase the solubility of the selected gaseous material in the perfluorochemical fluid.

Preferably, the apparatus includes a second conduit for transferring the perfluorochemical fluid between the treatment chamber and the reservoir. In addition, the apparatus preferably includes a circulation means for circulating the perfluorochemical fluid between the treatment chamber and the reservoir.

Further, in one aspect of the present invention, the apparatus preferably includes a heater for warming the perfluorochemical fluid.

In another aspect of the present invention, the apparatus includes a phase change apparatus for changing the physical state of the perfluorochemical fluid supplied to the treatment chamber. Preferably, the phase change apparatus is selected from the group consisting of nebulizers, aerosolizers, and vaporizers.

In another aspect of the present invention, the apparatus includes at least one port for providing a biologically active material in the perfluorochemical fluid.

In yet another aspect of the present invention, the apparatus includes at least one pressure reduction means for reducing the pressure of the perfluorochemical fluid.

Preferably, the apparatus also includes at least one sensor for sensing at least one physical property of the perfluorochemical fluid. Preferably, at least one sensor is adapted to sense the pressure of the perfluorochemical fluid. In another aspect, it is preferred that the at least one sensor be adapted to sense the temperature of the perfluorochemical fluid.

Preferably, the apparatus provides a means to control the circulation of the perfluorochemical fluid, as well as a means for controlling at least one property of the perfluorochemical fluid.

In one presently preferred embodiment of the present invention, the treatment chamber of the apparatus is sized and adapted to receive the entire body of the subject living organism, and the apparatus further includes a means for permitting a subject to respire.

In another presently preferred embodiment, the apparatus of the present invention includes a treatment chamber sized and adapted to receive a portion of the body of the living organism, and the treatment chamber includes at least one opening to receive the body portion, and at least one seal for sealing the at least one opening to the body. In one aspect, the treatment chamber is preferably adapted to receive a foot. In another aspect, the treatment chamber is preferably adapted to receive a portion of a limb.

DETAILED DESCRIPTION

The present invention provides a process to promote the healing of an area of the body of a subject living organism, such as a mammal, bird or reptile, affected by an injury or disease. In another aspect, the process of the present invention promotes musculoskeletal fatigue recovery. In yet another aspect, present invention provides a process for treating a portion of a living organism, such as an organ, tissue or cell(s) thereof. The present invention also provides apparatus for practicing the process of the present invention.

Figure 1:
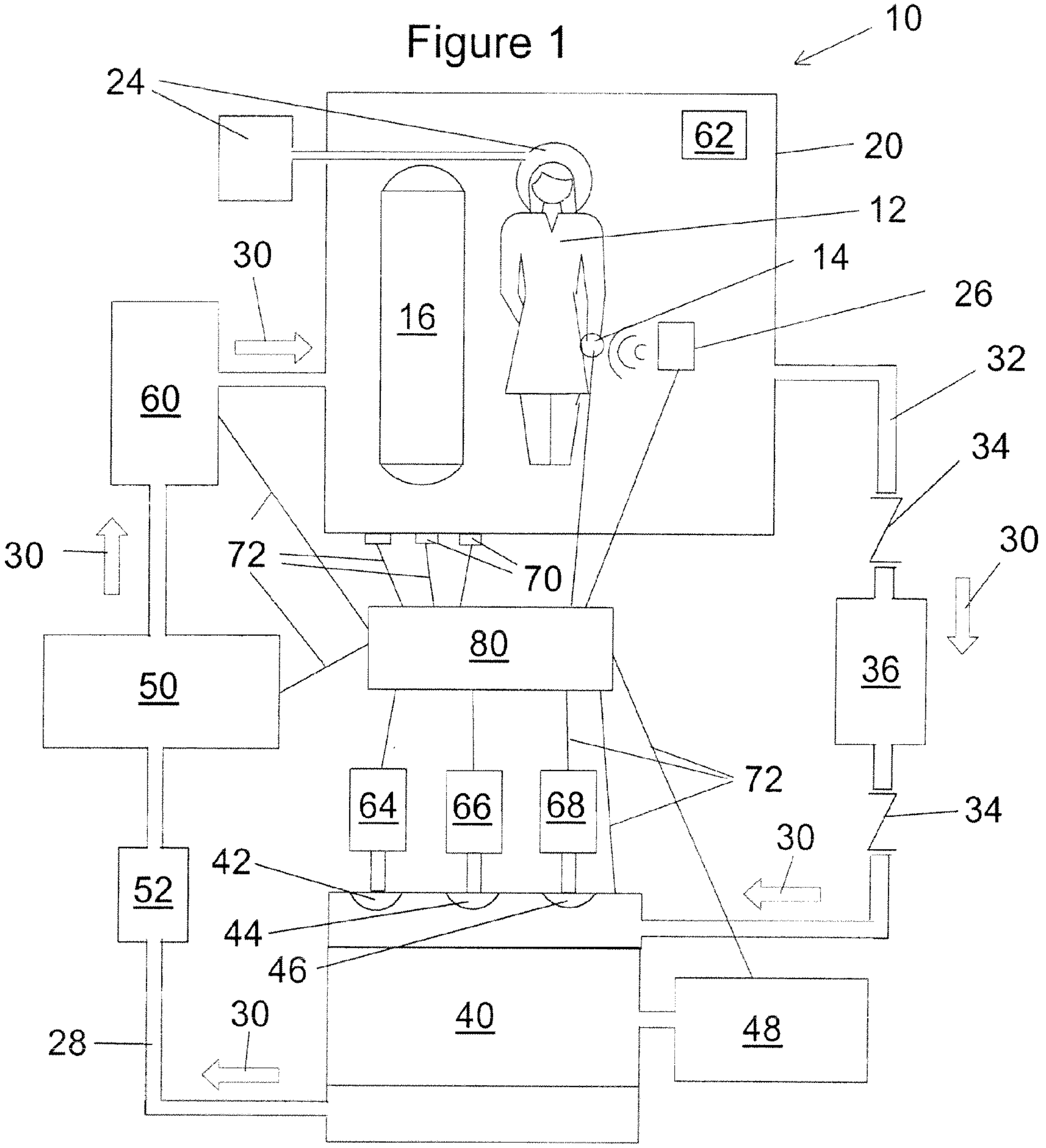
FIG. 1 is a schematic illustration of a first embodiment of a treatment apparatus according to the present invention.

Referring now to the figures in which like reference numerals represent like elements in each of the several views, there is shown in FIG. 1 a schematic illustration of a first embodiment of a treatment apparatus 10 according to the present invention. The treatment apparatus 10 is adapted to receive and contain the whole body of at least one subject 12 with an injury or a disease within a sealable clinical chamber 20. The treatment apparatus 10 includes suitable ventilation apparatus 24 or means for permitting the subject 12 to respire (including a face mask) within the sealed clinical chamber 20. This permits the subject to breathe ambient air or a predetermined gaseous mixture of oxygen and other gases at varying concentrations as clinically appropriate. Alternatively, the clinical chamber 20 can include a sealable port (not shown) so that the subject 12 can be positioned with most of his or her body in the chamber 20 other than his or her head. Suitable sensors 14 are provided for monitoring physiological properties of the subject 12, such as blood pressure, heart rate, etc. The clinical chamber 20 includes a sealable door 16 for permitting entry and egress of the subject 12. The clinical chamber 20 is also provided with a ultrasound source 26 for supplying ultrasound through the liquid perfluorochemical fluid, at frequencies presently employed for physical therapy of soft tissue or organ injuries.

The treatment apparatus 10 also includes a first conduit 28 for transferring perfluorochemical fluid between a reservoir 40 and the clinical chamber 20 in the direction shown by the arrows 30.

A second conduit 32 is provided for transferring perfluorochemical fluid between the clinical chamber 20 and the reservoir 40, and suitable valves are provided 34 such that the perfluorochemical fluid circulates through the treatment apparatus 10 in the direction shown by the arrows 30. In addition, the treatment apparatus 10 can optionally include suitable pump 36 for withdrawing the perfluorochemical fluid from the clinical chamber 20, and thereby reducing the pressure of the perfluorochemical fluid inside the clinical chamber 20, and circulating the perfluorochemical fluid.

The reservoir 40 includes several ports 42, 44, 46 for injecting or adding substances, such as gaseous substances such as oxygen, into the perfluorochemical fluid. A compressor 48 is provided to increase the pressure of the perfluorochemical fluid.

Thus, the treatment apparatus 10 of present invention provides pressurization of the environment (hyperbaric conditions) provided in the clinical chamber 20 to greater than one atmosphere to promote oxygenation of the perfluorochemical fluid and thus the tissues of the subject 12. Further, the treatment apparatus 10 of present invention provides for depressurizing the environment (hypobaric conditions) provided in clinical chamber 20.

The treatment apparatus 10 also includes a phase change apparatus 50 which is adapted to provide the perfluorochemical fluid to the clinical chamber 10 in a preferred physical form, such as by atomizing, nebulizing, or vaporizing the perfluorochemical fluid. In addition, a temperature control means 60, such as a heater, heating coils and/or cooling coils, is provided to adjust the temperature of the perfluorochemical fluid being provided to the clinical chamber 20. Thus, the present invention provides for warming of the perfluorochemical fluid to above the body temperature of subject 12 to increase perfusion and oxygenation to the injury site. A pressure reduction means such as a relief valve 62 is also provided to reduce the pressure of the perfluorochemical fluid in the clinical chamber 20 if desired.

The treatment apparatus 10 further includes a gas injection device 64 for injecting gas, such as oxygen, helium or nitric oxide, into the perfluorochemical fluid. The present invention thus provides for the addition of other gases to oxygen to improve tissue oxygenation in appropriate clinical settings. For instance, gases such as helium, nitric oxide, etc. could potentially promote better delivery, tissue perfusion and thus, oxygenation of the tissue site. In other applications of the treatment apparatus 10, such as in promoting vegetative growth, carbon dioxide can be substituted for oxygen.

The treatment apparatus 10 also includes a fluid injection device 66 for injecting fluids such as pharmaceutically active or biologically active fluids into the perfluorochemical fluid, and a particulate injection device 68 for injecting particulates such as pharmaceutically active particulates, for example, magnetically charged particles, into the perfluorochemical fluid. Thus the present invention provides for administration of pharmaceutical and/or biological agents and chemicals to the perfluorochemical fluid including but not limited to tissue growth promoters, hormones, antibiotics, genetic therapy delivery systems, etc. to promote tissue healing.

The properties of the perfluorochemical fluid can also be adjusted by a filtration device 52, which can include a microfiltration membrane to provide electrically charged particles in the perfluorochemical fluid. Thus, the present invention optionally provides, where clinically indicated, for the development of an electrically charged particles in the perfluorochemical environment, obtained via circulating the perfluorochemical through a microfiltration membrane. Alternatively, or in addition, where clinically indicated magnetically charged particles can be added to the perfluorochemical fluid.

Physical properties of the perfluorochemical fluid such as the temperature and pressure of the perfluorochemical fluid inside the treatment chamber 20 are monitored by suitable sensors 70. The output of the sensors 70 is transmitted through data lines 72 to a control unit 80 which monitors key operating parameters of the treatment apparatus 10 and controls the operation of the various elements of the treatment apparatus 10 including the injection devices 64, 66, 68, the compressor 48, the phase change apparatus 50, and the temperature control means 60 through suitable data and control lines 72. In addition, the output of the sensors 14 monitoring the physiological properties of the subject 12 is fed to the control unit 80. The control unit 80 controls operation of the treatment apparatus 10 according to a predetermined program. For example, the control unit 80 can be used to bring the circulation of the perfluorochemical fluid through the treatment apparatus 10 to a steady state, to periodically inject oxygen into the circulating perfluorochemical fluid, to raise and lower the pressure of the perfluorochemical fluid in the clinical chamber 20 in a predetermined manner, etc. The control unit 80 can include conventional data acquisition devices such as A/D converters, peripheral device control units such as D/A converters, suitable real time data processing and control capabilities including dedicated microprocessors, and provision for remote monitoring of the treatment apparatus 10, as well as a suitable operator interface to permit continuous monitoring and control of key variables.

Figure 2:
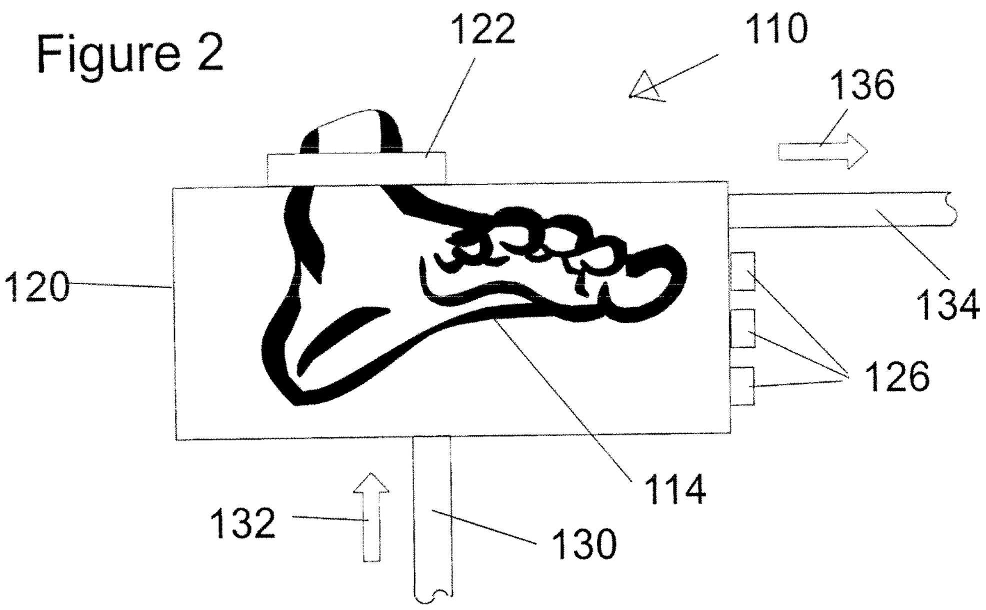
FIG. 2 is a schematic illustration of a portion of a second embodiment of a treatment apparatus according to the present invention.

A schematic view of a second embodiment of a treatment apparatus 110 according to the present invention is shown in FIG. 2. In this embodiment, the clinical chamber 120 includes a single seal 122 for receiving a portion of a subject's body, such as a foot 114 affected with an ischemic ulcer, within the clinical chamber 120. Perfluorochemical fluid is provided by a first conduit 130 to the clinical chamber 120 and is withdrawn from the clinical chamber 120 through a second conduit 134, such that the perfluorochemical fluid circulates through the clinical chamber 120 in the direction of the arrows 132, 136. Properties of the perfluorochemical fluid in the clinical chamber 120 are monitored by a plurality of suitable sensors 126.

In this embodiment, the foot 114 is placed in clinical chamber 120 and sealed mechanism above the level of injury to prevent leakage of the perfluorochemical fluid while maintaining optimal pressurization, such as with an adhesive seal to the skin of the subject above the ankle. As in the case of the first embodiment, in this second embodiment the treatment apparatus 110 provides a continuous circulating flow of perfluorochemical fluid interposed between the foot and the wall of the clinical chamber 120. The perfluorochemical fluid enters and leaves the chamber 120 via the first and second conduits 130, 134 through respective intake and exit ports. The pressure of the perfluorochemical fluid is maintained using an in-line compressor (not shown), with an internal pressure sensor (not shown) to provide pressurization levels within the circuit. A separate container (not shown) of perfluorochemical fluid is employed as a reservoir for the fluid. This reservoir serves as the source of the perfluorochemical fluid transferred to the clinical chamber 120 and also serve as a receptacle for the perfluorochemical fluid exiting the clinical chamber 120, forming a closed circuit, and a recycling system for the fluid. The reservoir also includes openings or ports to allow for addition of drugs and other additives as discussed above. In addition, nebulization, vaporization, or aerosolization units (not shown) can be interposed between the reservoir and the container to deliver the fluid in the desired phase. Once a predetermined concentration of perfluorochemical fluid and optimal pressurization has been achieved, the apparatus can be operated under steady state closed circuit conditions for a desired time period. An integrated microprocessor (not shown) can be employed to regulate all parameters including but not limited to temperature, fluid phase, pressure, perfluorochemical concentration, oxygen concentration, other gas concentrations, etc.

Figure 3:
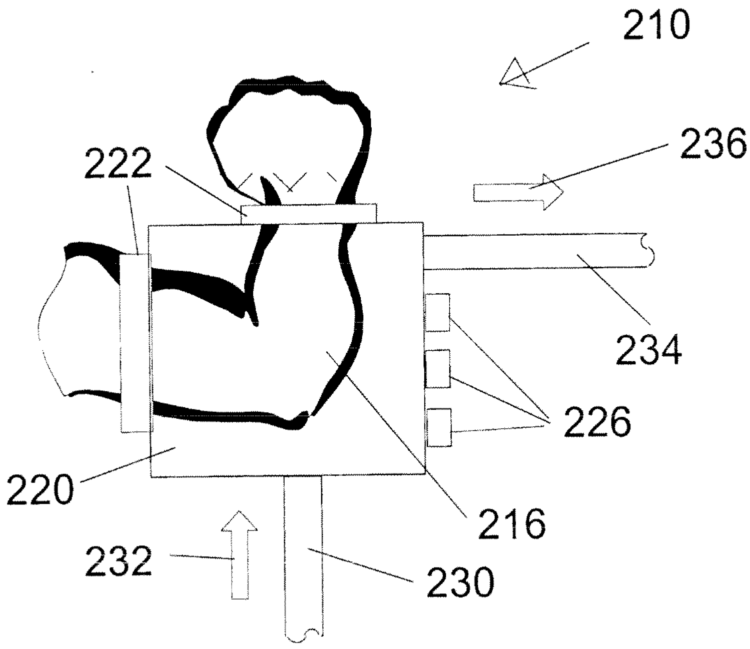
FIG. 3 is a schematic illustration of a portion of a third embodiment of a treatment apparatus according to the present invention.

A schematic view of a third embodiment of a treatment apparatus 210 according to the present invention is shown in FIG. 3. In this third embodiment, the clinical chamber 220 includes a pair of seals 222 for receiving a portion of a subject's body, such as an elbow 216, within the clinical chamber 220. Perfluorochemical fluid is similarly provided by a first conduit 230 to the clinical chamber 220 and is withdrawn from the clinical chamber 220 through a second conduit 234, such that the perfluorochemical fluid circulates through the clinical chamber 220 in the direction of the arrows 232, 236. In addition, the properties of the perfluorochemical fluid in the clinical chamber 220 are monitored by a plurality of suitable sensors 226.

The present invention further contemplates that any and all body parts could be treated using a suitable preformed chamber with appropriate seals to accommodate the particular anatomy, including the thorax, abdomen, and spine.

In addition, the present invention provides for enlarged clinical chambers (not shown) designed for multiple subjects, such as from four to eight subjects. In this case, therapeutic wands are provided (not shown) for delivery of perfluorochemical fluid to specific, predetermined regions of a subject's anatomy to emphasize, localize, and individualize treatment with the perfluorochemical fluid, while the entire bodies of each of the subjects receive the benefit of exposure to the perfluorochemical fluid.

Thus, the process of the present invention can be applied either to localized regions of the body such as individual limbs, joints, etc. or in the form of total body exposure in a chamber while the subject or patient is exposed to normal respiratory gas breathing mixtures and the rest of the subject's body is being exposed to the perfluorochemical fluid.

Thus, in the process of the present invention, the subject (or a portion of the subject) is put into a closed environment, and a perfluorochemical fluid is provided in the closed environment. The perfluorochemical fluid is preferably circulated through the closed environment. Preferably, the perfluorochemical fluid comprises at least one fluorinated hydrocarbon having at least one-half of the corresponding hydrocarbon's hydrogen atoms substituted by fluorine. The at least one fluorinated hydrocarbon is preferably selected from the group consisting of $C_4F_9CH{=}CH_4C_9$, i-$C_3F_9CH{=}CHC_6F_{13}$, $C_6F_{13}CH{=}CHC_6F_{13}$, $C_{10}F_{18}$, $C_8F_{17}Br$, $(C_6F_{13})_2O$, $CF_3CFOCF_2CF_3$, $(CF_3)_2CFO(CF_2)_3CF_3$, $(CF_3)_2CFO(CF_2)_4OCF(CF_3)_2$, $(CF_3)_2CFO(CF_2)_6OCF(CF_3)_2$, F-2-butyltetrahydrofuran, F-n-cyclohexylpyrrolidine, F-n-methyldecahydroquinoline, F-n-methyldecahydroisoquinoline, F-adamantane, F-methyladamantane, F-1,3-dimethyladamantane, F-dimethylbicyclo[3,3,1]nonane, F-trimethylbicyclo[3,3,1]nonane, F-tripropylamine, F-tributylamine, C-4 alkyl decalins $C_{14}F_{24}/C_{14}F_{26}$, $C_{10}F_{18}$, $C_8F_{17}Br$, $C_6F_{14}$-perfluorohexanes, and mixtures thereof. Suitable perfluoro compounds are also disclosed in U.S. Pat. Nos. 4,105,798; 4,110,474; 4,187,252; 4,289,499; 4,443,480; RE 33,451; 5,514,720; 5,635,539; 5,684,050; 5,674,913; 5,824,703; 5,840,767, and 6,343,225, each incorporated herein by reference.

A selected gaseous material, such as oxygen, is dissolved in the perfluorochemical fluid, and the subject, or a portion of the subject, is immersed in the perfluorochemical fluid in which the selected gaseous material is dissolved. The pressure within the closed environment is preferably adjusted to differ from the atmospheric pressure. Thus, the present process provides submersion, immersion, or envelopment of an affected area or body part using a biomedical device with an oxygenated perfluorochemical fluid, in a liquid, nebulized, vaporized or aerosolized phase.

Thus, in one aspect the present invention provides a process to promote the healing of an area of the body of a living organism affected by an injury or disease. This process comprises confining the affected area in a closed environment, and providing a perfluorochemical fluid in the closed environment. In this process, oxygen is dissolved in the perfluorochemical fluid to oxygenate the perfluorochemical fluid, and a pressure differing from atmospheric pressure is provided in the closed environment. In this process, the affected area is treated by immersing the area in the oxygenated perfluorochemical fluid.

In one embodiment of this aspect of the present invention, the process of the present invention provides hypobaric conditions, specifically, below one atmospheric pressure. In this embodiment, the high capacitance of perfluorochemical fluids for carbon dioxide is employed to promote the extraction of carbon dioxide from the body of the subject, thus reducing the local tissue acidosis that at time delays healing and otherwise promotes inflammation. The process of the present invention can be employed to provide full hypobaric sessions in order to reduce local tissue acidosis in wounds and injuries. The process of the present invention also provides therapy sessions with alternating hyper and hypobaric environments.

The present invention can be employed in treating a variety of diseases and injuries. In one embodiment the process of the present invention is used to provide both hyperbaric and hypobaric conditions for anti-cancer therapy. It is well established that local invasion by tumors into normal tissues is mediated by local tissue acidosis created by tumors (via anaerobic glycolysis) that give them a competitive survival advantage over contiguous normal tissue. The process of the present invention can be used to reduce local tissue acidosis in order to alter local microenvironmental factors around tumors, with the goal of reducing tumor invasion and potentially reversing the competitive advantage that such invasive tumors have against contiguous normal tissues, resulting in the shrinkage of such tumors. Preferably, in this embodiment of the process anti-tumor agents are added to the perfluorochemical fluid.

In yet another embodiment, the present invention provides improved physical therapy to a subject. In this embodiment, the clinical chamber 20 is filled to a predetermined level with perfluorochemical fluid in liquid form, and predetermined portions of the subject's body are provided with resistive loading using conventional physical therapy equipment (not shown). Perfluorochemical fluids typically have a substantially higher specific gravity than water (about twice) and therefore provide greater buoyancy and a concomitantly greater reduction in the gravitational load perceived by the immersed subject. Perfluorochemical fluids also typically have a greater viscosity than water (2-3×), and therefore offer greater resistive loading during physical therapy procedures. Finally, process of this invention advantageously provides the injured site elevated oxygen delivery and carbon dioxide removal, while simultaneously heating the site to provide increased perfusion of the perfluorochemical fluid.

For certain physical therapy procedures in conventional exercise tanks, the injured site could be deprived of adequate gas exchange, thus making the therapy less than optimal. However, by providing enhanced transdermal gas exchange, the present invention provides an accelerated level of rehabilitation even in the face of poor systemic gas exchange to the injury site. The clinical chamber of the present invention can be varied in size and shape, and type of resistive loading, depending on the injury and anatomy of the patient.

In this embodiment, the process and apparatus of present invention can not only be used for injuries, but could also to promote musculoskeletal (muscle, tendon, ligament, cartilage, etc) fatigue recovery after strenuous activity (e.g. —high activity sports) for athletes.

In yet another embodiment, the process of the present invention is employed to treat mycotic (fungal) infections of the nails, as well as a wide variety of other nail and nailbed disorders including nail pitting, cracking, and other nail infections. Formerly, therapy for mycotic infections required systemic administration of antifungal agents with significant toxicity that requires constant liver function and other blood test monitoring due to hepatic and other toxicities of treatment agents. The process and apparatus of the present invention can be employed, with the optional addition of anti-fungal agents to the perfluorochemical fluid, to treat such disorders for medical and/or cosmetic purposes by increased oxygenation, local carbon dioxide reduction, increased blood flow in nailfold capillaries and pressurized topical delivery of anti-fungal agents (and other biological agents) into nails and nailbeds, resulting in improved nail health and appearance.

In the process and apparatus of the present invention, the pressure of the perfluorochemical fluid can be varied over time according to a predetermined program, such as by cycling the pressure between hyperbaric conditions and hypobaric conditions. Under certain conditions, as in the case of single extremity units as shown in FIG. 2, hyperbaric pressures could potentially decrease local perfusion to an enclosed limb over time. Accordingly, hyperbaric conditions could be alternated with normal or hypobaric states within the treatment chamber to provide varying pressure upon the subject's tissues. The specific pressure cycling program employed in the present process is determined by a variety of factors, including the oxygen needs of the involved tissues, vascular supply to the target tissues, oxygen demands for wound healing, etc.

For example, the specific pressure cycling program can employ cardiac gating, such that the variation of pressure is synchronized with cardiac rhythms (systole and diastole) to maximize beneficial effects. Alternatively, experimentally derived periodicity of alternating pressures can be used, depending upon the desired clinical effect.

In another embodiment, the present invention provides a process for treating subject living cells, such as in the form of cultured tissues, organs for transplantation such as hearts, tissues for transplantation or research such as heart value tissues and cartilage structures, cell cultures such as stem cell cultures, as well as multicellular and single cell organisms such as fungi and bacteria.

Various modifications can be made in the details of the various embodiments of the processes, compositions and articles of the present invention, all within the scope and spirit of the invention and defined by the appended claims.

What is claimed is:

1. A process for treating a subject living organism, the process comprising:

(a) confining at least a portion of the organism in a closed environment;

(b) providing a circulating perfluorochemical fluid in the closed environment;

(c) dissolving a selected gaseous material in the perfluorochemical fluid to provide perfluorochemical fluid containing the dissolved selected material;

(d) providing a pressure differing from atmospheric pressure in the closed environment;

(e) immersing the at least a portion of the organism in the perfluorochemical fluid containing the selected gaseous material; and (f) alternately pressurizing the closed environment to a first pressure and a second pressure, in a cycled manner, the pressure cycling employing cardiac gating, such that the variation of pressure is synchronized with cardiac rhythms.

2. The process according to claim 1 further comprising controlling the temperature of the closed environment.

3. The process according to claim 1 wherein the process is employed to promote the healing of an area of the body of a living organism affected by injury or disease, at least the affected area is confined in the closed environment, and the selected gaseous material is oxygen.

4. The process according to claim 1 further comprising varying the pressure according to a predetermined pressure variation program.

5. The process according to claim 2 further comprising varying the temperature of the closed environment according to a predetermined temperature variation program.

6. The process according to claim 1 further comprising providing a biologically active material in the perfluorochemical fluid.

7. The process according to claim 6 wherein the biologically active material is selected from the group consisting of tissue growth promoters, hormones, antibiotics, genetic delivery systems, and pharmaceutical delivery systems.

8. The process according to claim 1 wherein the perfluorochemical fluid is provided in a fluid form selected from the group consisting of liquid, nebulized, vaporized and aerosolized phases.

9. The process according to claim 1 wherein the perfluorochemical fluid comprises at least one fluorinated hydrocarbon having at least one-half of the corresponding hydrocarbon's hydrogen atoms substituted by fluorine.

10. The process according to claim 9 wherein at least one fluorinated hydrocarbon is selected from the group consisting of $C_4F_9CH{=}CH_4C_9$, i-$C_3F_9CH{=}CHC_6F_{13}$, $C_6F_{13}CH{=}CHC_6F_{13}$, $C_{10}F_{18}$, $C_8F_{17}Br$, $(C_6F_{13})2O$, $CF_3CFOCF_2CF_3$, $(CF_3)_2CFO(CF_2)_3CF_3$, $(CF_3)_2CFO(CF_2)_4OCF(CF_3)_2$, $(CF_3)_2CFO(CF_2)_6OCF(CF_3)_2$, F-2-butyltetrahydrofuran, F-n-cyclohexylpyrrolidine, F-n-methyldecahydroquinoline, F-n-methyldecahydroisoquinoline, F-adamantane, F-methyladamantane, F-1,3-dimethyladamantane, F-dimethylbicyclo[3,3,1]nonane, F-trimethylbicyclo[3,3,1]nonane, F-tripropylamine, F-tributylamine, C-4 alkyl decalins $C_{14}F_{24}/C_{14}F_{26}$, $C_{10}F_{18}$, $C_8F_{17}Br$, $C_6F_{14}$-perfluorohexanes, and mixtures thereof.

11. The process according to claim 1 further comprising providing electrically charged particles in the perfluorochemical fluid.

12. The process according to claim 1 further comprising providing magnetically charged particles into the perfluorochemical fluid.

13. The process according to claim 1 further comprising dissolving other therapeutic gases in the perfluorochemical fluid to enhance the oxygenation of the perfluorochemical fluid.

14. The process according to claim 13 wherein other gases are selected from the group consisting of helium, nitric oxide, and other therapeutic gases.

15. The process according to claim 1 further comprising transmitting ultrasound through the liquid perfluorochemical fluid to the affected area, the ultrasound having a frequency selected from those employed in established practice for physical therapy of soft tissue or organ injuries.

16. The process according to claim 1 wherein the entire living organism is confined in the closed environment and further comprising providing respiration means to the living organism.

17. The process according to claim 1 wherein a portion of the living organism is confined in the closed environment.

* * * * *

UNITED STATES PATENT AND TRADEMARK OFFICE

CERTIFICATE OF CORRECTION

PATENT NO. : 8,535,691 B2
APPLICATION NO. : 11/276180
DATED : September 17, 2013
INVENTOR(S) : Thomas H. Shaffer, Robert G. Stern and Marla R. Wolfson It is certified that error appears in the above-identified patent and that said Letters Patent is hereby corrected as shown below:

In the Specification

Column 9, line 28, reads “Finally, process of this invention  advantageously provides the”

should read -- Finally, because perfluoro chemical fluids have high oxygen and carbon dioxide solubility, the process of this invention advantageously provides the injured site --

Signed and Sealed this
Fifth Day of November, 2013

Teresa Stanek Rea
*Deputy Director of the United States Patent and Trademark Office*